(12) United States Patent
Nieuwstadt et al.

(10) Patent No.: US 6,925,796 B2
(45) Date of Patent: Aug. 9, 2005

(54) DIAGNOSIS OF A UREA SCR CATALYTIC SYSTEM

(75) Inventors: Michiel van Nieuwstadt, Ann Arbor, MI (US); Devesh Upadhyay, Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 3 days.

(21) Appl. No.: 10/716,137

(22) Filed: Nov. 19, 2003

(65) Prior Publication Data

US 2005/0103000 A1    May 19, 2005

(51) Int. Cl.[7] ............................................... F01N 3/00
(52) U.S. Cl. ............................. 60/277; 60/274; 60/276
(58) Field of Search ............................ 60/274, 276, 277

(56) References Cited

U.S. PATENT DOCUMENTS

| | | | |
|---|---|---|---|
| 5,201,802 A | | 4/1993 | Hirota et al. |
| 5,426,934 A | * | 6/1995 | Hunt et al. .................... 60/276 |
| 5,709,080 A | | 1/1998 | Arora et al. |
| 5,953,907 A | * | 9/1999 | Kato et al. ..................... 60/274 |
| 6,112,518 A | * | 9/2000 | Jerger et al. ................... 60/274 |
| 6,134,883 A | * | 10/2000 | Kato et al. ..................... 60/274 |
| 6,145,305 A | * | 11/2000 | Itou et al. ...................... 60/277 |
| 6,167,695 B1 | | 1/2001 | Itou et al. |
| 6,185,929 B1 | * | 2/2001 | Ishizuka et al. ............... 60/274 |
| 6,216,451 B1 | | 4/2001 | Schnaibel et al. |
| 6,305,160 B1 | | 10/2001 | Hammerle et al. |
| 6,434,928 B1 | * | 8/2002 | Manaka ....................... 60/274 |

* cited by examiner

*Primary Examiner*—Thomas Denion
*Assistant Examiner*—Diem Tran
(74) *Attorney, Agent, or Firm*—Julia Voutyras; Allan J. Lippa

(57) ABSTRACT

A method for diagnosing degradation in a pair of NOx sensors coupled upstream and downstream of a NOx catalyst is presented. The method is performed when catalyst temperature is such that its NOx conversion efficiency is substantially zero, such as when the catalyst temperature is very low (at cold start) or very high (e.g., following regeneration). Under those conditions, sensor degradation can be diagnosed if the upstream and downstream NOx sensor readings are not substantially the same.

9 Claims, 4 Drawing Sheets

DIAGNOSIS OF A UREA SCR CATALYTIC SYSTEM

FIELD OF INVENTION

The present invention relates to a system and a method for diagnosing degradation in a lean exhaust gas aftertreatment system, and more particularly to diagnosing degradation of the NOx sensors coupled upstream and downstream of a NOx catalyst.

BACKGROUND OF THE INVENTION

Current emission control regulations necessitate the use of catalysts in the exhaust systems of automotive vehicles in order to convert carbon monoxide (CO), hydrocarbons (HC), and nitrogen oxides (NOx) produced during engine operation into unregulated exhaust gasses. Vehicles equipped with diesel or other lean burn engines offer the benefit of increased fuel economy, however, catalytic reduction of NOx emissions via conventional means in such systems is difficult due to the high content of oxygen in the exhaust gas. In this regard, Selective Catalytic Reduction (SCR) catalysts, in which NOx is continuously removed through active injection of a reductant, into the exhaust gas mixture entering the catalyst, are known to achieve high NOx conversion efficiency. Typically, reductant, such as aqueous urea, is carried on board of a vehicle, and an injection system is used to supply it into the exhaust gas stream entering the SCR catalyst where it decomposes into hydro cyanic acid (HNCO) and gaseous ammonia ($NH_3$). The amount of reductant injection is usually determined based on operating conditions, such as engine speed, load, catalyst temperature, and on the NOx conversion efficiency of the catalyst, which can be monitored by coupling a pair of NOx sensors upstream and downstream of the SCR catalyst.

The inventors herein have recognized that in order to achieve high NOx conversion efficiency in such systems, it is important to accurately and quickly diagnose degradation of the upstream and downstream NOx sensors. The inventors have further recognized that under some operating conditions, such as when the SCR catalyst is very cold or very hot, its NOx conversion efficiency is substantially zero. Therefore, under those circumstances, the NOx sensor readings upstream and downstream of the catalyst are expected to be substantially the same.

SUMMARY OF THE INVENTION

Accordingly, the present invention is directed to a method for diagnosing degradation of a lean exhaust gas aftertreatment system, the system including a NOx catalyst having a first NOx sensor coupled upstream of the catalyst and a second NOx sensor coupled downstream of the catalyst, the method comprising: comparing a first NOx sensor measurement and a second NOx sensor measurement when a catalyst temperature is within a first predetermined temperature range, and providing an indication of system degradation when a difference between said first NOx sensor measurement and said second sensor measurement is greater than a second predetermined value.

In accordance with one embodiment of the present invention, the NOx catalyst is a urea-based Selective Catalytic Reduction (SCR) catalyst. In another embodiment of the present invention, the NOx catalyst is an Active Lean NOx (ALNC) catalyst. In yet another embodiment of the present invention, the NOx catalyst is a Lean NOx Trap (LNT).

In another embodiment of the present invention, an indication of system degradation comprises indicating a first NOx sensor degradation if a difference between said first NOx sensor reading and an estimate of an amount of NOx in an exhaust gas mixture entering the catalyst is greater than a third predetermined value and indicating a second NOx sensor degradation otherwise.

Thus, with such an arrangement, if the catalyst temperature is such that its NOx conversion efficiency is substantially zero, system degradation can be diagnosed if the NOx sensor measurements upstream and downstream of the catalyst are not substantially equal. Additionally, once system degradation is diagnosed, the upstream NOx sensor can be identified as a source of degradation if the difference between an estimated amount of NOx in an exhaust gas mixture entering the catalyst and the first NOx sensor measurement is greater than expected. Otherwise, if the upstream NOx sensor is not degraded, degradation of the downstream NOx sensor is indicated.

In yet another aspect of the present invention, method for diagnosing degradation of a NOx sensor coupled downstream of a NOx catalyst, includes: estimating an amount of NOx in an exhaust gas mixture entering the catalyst based on operating conditions; comparing said estimate to a NOx sensor signal when a catalyst temperature is within a predetermined operating range; and providing an indication of the NOx sensor degradation based on a result of said comparison.

Thus, with such an arrangement, downstream NOx sensor degradation can be diagnosed by comparing an estimate of an amount of NOx upstream of the catalyst to the NOx sensor reading downstream of the catalyst when catalyst temperature is such that its NOx conversion efficiency is substantially zero.

An advantage of the above aspect of invention is improved system diagnostics. Yet another advantage of the present invention is improved NOx conversion efficiency.

The above advantages and other advantages, objects and features of the present invention will be readily apparent from the following detailed description of the preferred embodiments when taken in connection with the accompanying drawings.

BRIEF DESCRIPTION OF THE DRAWINGS

The objects and advantages described herein will be more fully understood by reading an example of an embodiment in which the invention is used to advantage, referred to herein as the Description of Preferred Embodiment, with reference to the drawings, wherein.

DESCRIPTION OF PREFERRED EMBODIMENT(S)

Figure 1A:
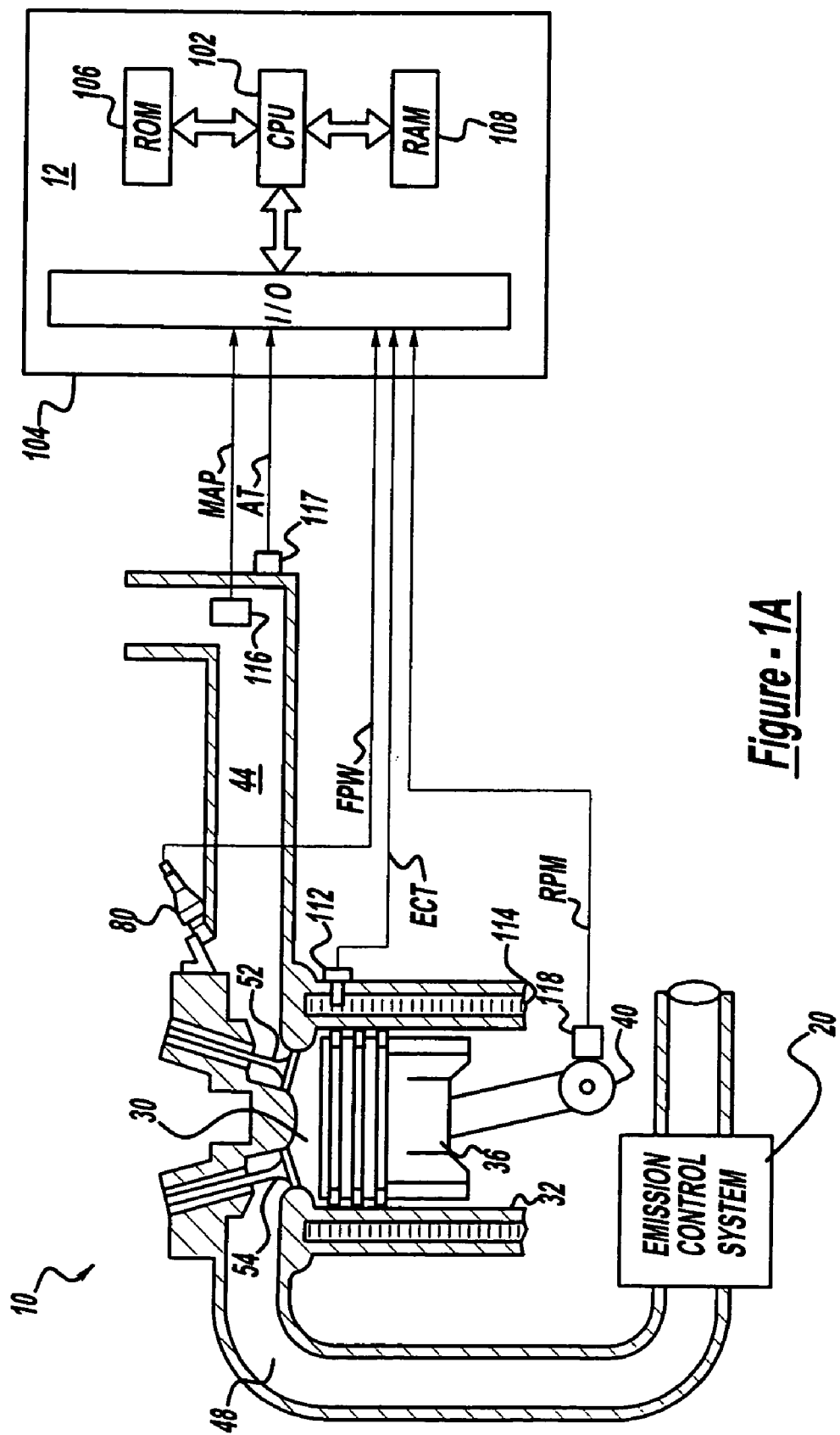
FIGS. 1A and 1B are schematic diagrams of an engine wherein the invention is used to advantage.

Internal combustion engine 10, comprising a plurality of cylinders, one cylinder of which is shown in FIG. 1, is controlled by electronic engine controller 12. Engine 10 includes combustion chamber 30 and cylinder walls 32 with piston 36 positioned therein and connected to crankshaft 40. Combustion chamber 30 is shown communicating with intake manifold 44 and exhaust manifold 48 via respective intake valve 52 and exhaust valve 54. Intake manifold 44 is also shown having fuel injector 80 coupled thereto for delivering liquid fuel in proportion to the pulse width of signal FPW from controller 12. Both fuel quantity, controlled by signal FPW and injection timing are adjustable. Fuel is delivered to fuel injector 80 by a fuel system (not shown) including a fuel tank, fuel pump, and fuel rail (not shown).

Controller 12 is shown in FIG. 1 as a conventional microcomputer including: microprocessor unit 102, input/output ports 104, read-only memory 106, random access memory 108, and a conventional data bus. Controller 12 is shown receiving various signals from sensors coupled to engine 10, in addition to those signals previously discussed, including: engine coolant temperature (ECT) from temperature sensor 112 coupled to cooling sleeve 114; a measurement of manifold pressure (MAP) from pressure sensor 116 coupled to intake manifold 44; a measurement (AT) of manifold temperature from temperature sensor 117; an engine speed signal (RPM) from engine speed sensor 118 coupled to crankshaft 40.

Figure 2:
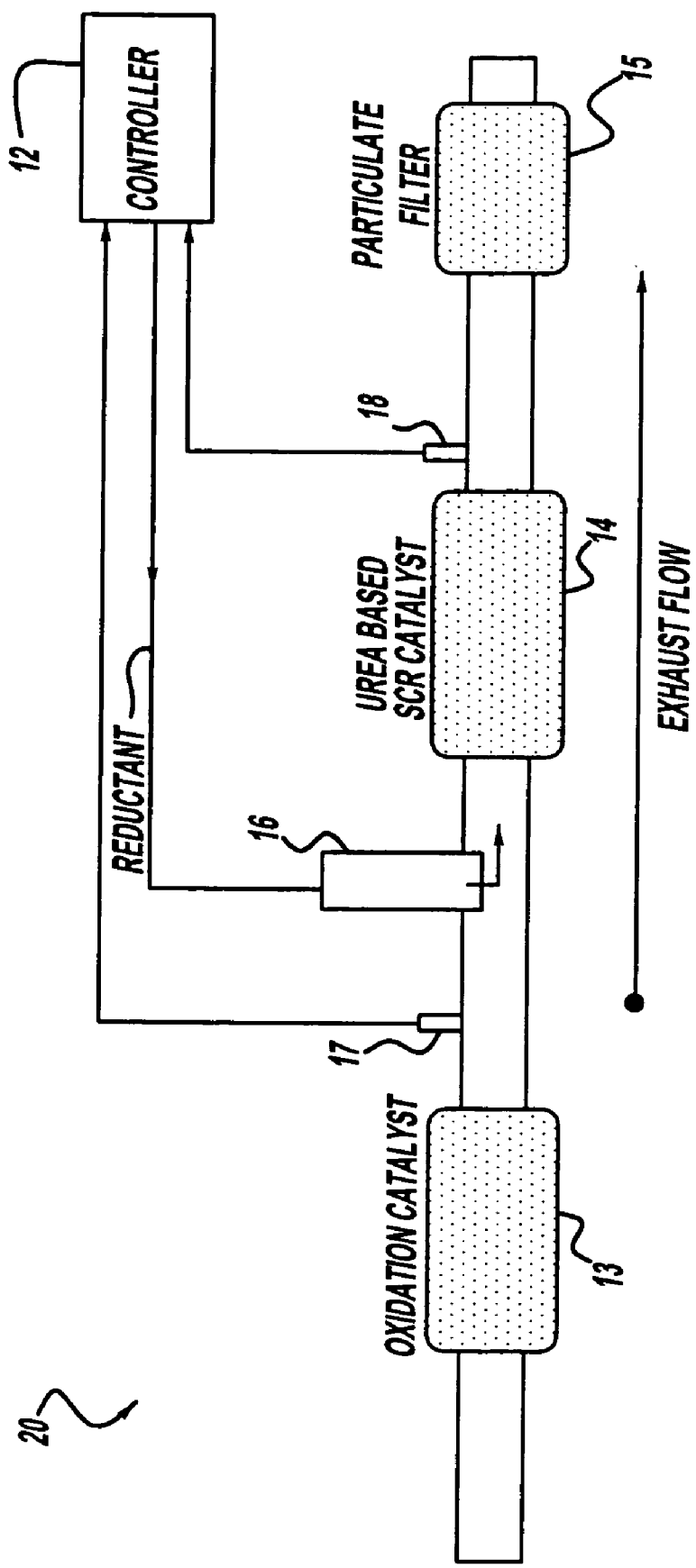
FIG. 2 is a an example of one embodiment of an emission control system wherein the present invention is used to advantage.

An emission control system 20 is coupled to an exhaust manifold 48 and is described with particular reference to FIG. 2.

Figure 1B:
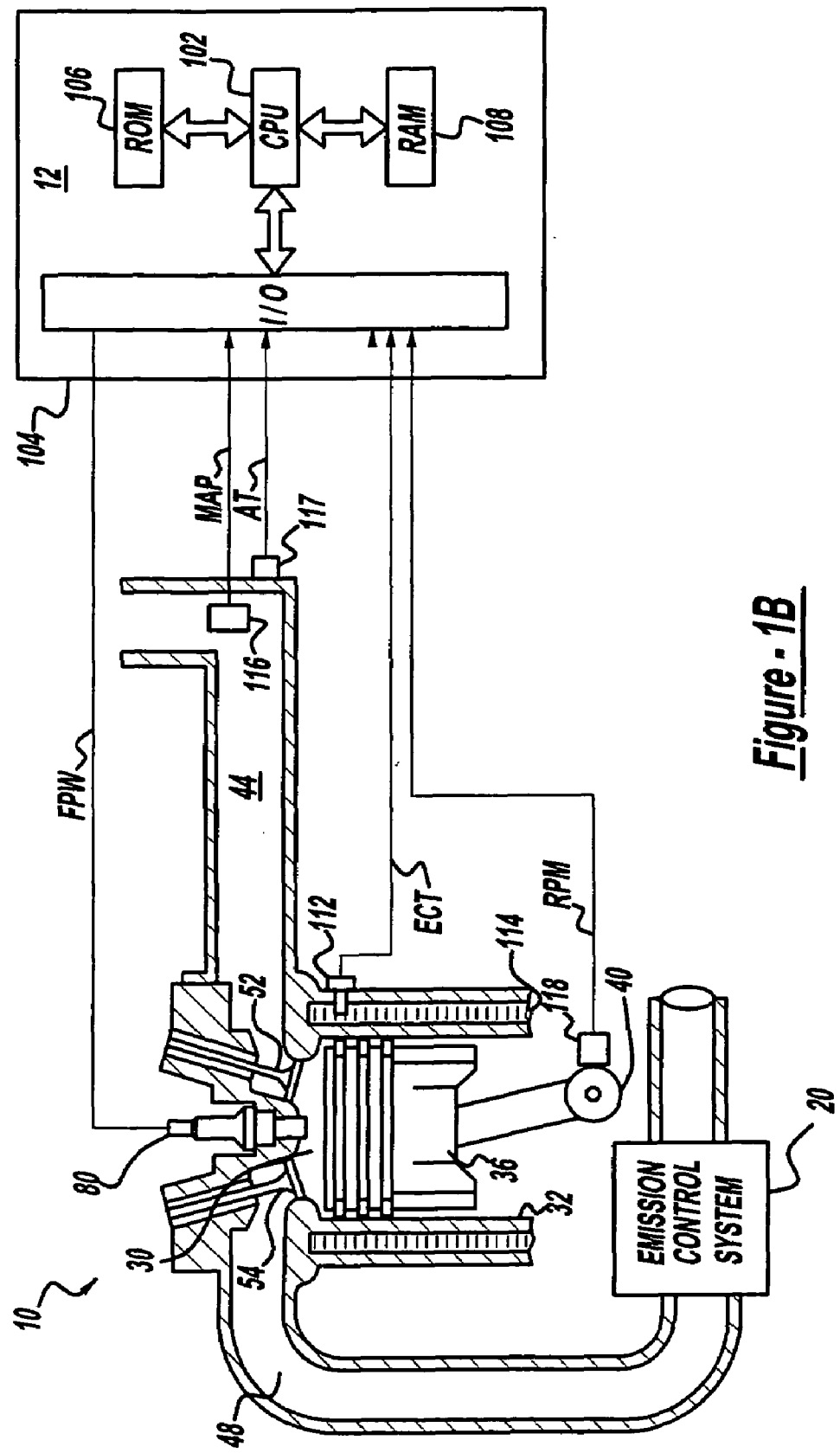

Referring now to FIG. 1B, an alternative embodiment is shown where engine 10 is a direct injection engine with injector 80 located to inject fuel directly into cylinder 30.

Referring now to FIG. 2, the emission control system 20 comprises a NOx catalyst 14, which in this embodiment is a urea-based Selective Catalytic Reduction (SCR) catalyst, capable of reducing NOx in an oxygen rich environment. Reductant, such as aqueous urea, is stored in a storage vessel (not shown) and delivered via a reductant injector 16 coupled to exhaust manifold 48 upstream of SCR catalyst 14. The reductant is metered out by a pump through a control valve (not shown) where both the pump and the valve are controlled by controller 12. Alternatively, any other means known to those skilled in the art to supply reductant to an exhaust gas aftertreatment device may be used. In an alternative embodiment, catalyst 14 may be an Active Lean NOx (ALNC) catalyst, and the reductant may be hydrocarbon. Two NOx sensors, $NOx_1$ (17) upstream and $NOx_2$ (18) downstream of the SCR are coupled in the path of the exhaust gas entering and exiting the SCR catalyst. The outputs of these sensors are read by controller 12 and may be used to estimate the NOx conversion efficiency of the SCR. Alternatively, $NOx_1$ sensor 17 can be eliminated and the amount of NOx in the exhaust gas mixture entering the SCR catalyst can be estimated based on engine speed, load, exhaust gas temperature or any other parameter known to those skilled in the art to affect engine NOx production.

Controller 12 also calculates the operating temperature of the SCR based on signals from temperature sensors coupled upstream, $T_{in}$, and downstream, $T_{out}$, of the catalyst (not shown). Alternatively, catalyst temperature may be determined by placing a temperature sensor mid-bed of the catalyst, or by any other means known to those skilled in the art to determine SCR catalyst temperature.

Oxidation catalyst 13 is coupled upstream of the SCR catalyst and may be a precious metal catalyst, preferably one containing platinum. The oxidation catalyst exothermically combusts hydrocarbons (HC) in the incoming exhaust gas from the engine thus supplying heat to rapidly warm up the SCR catalyst 14.

Figure 3:
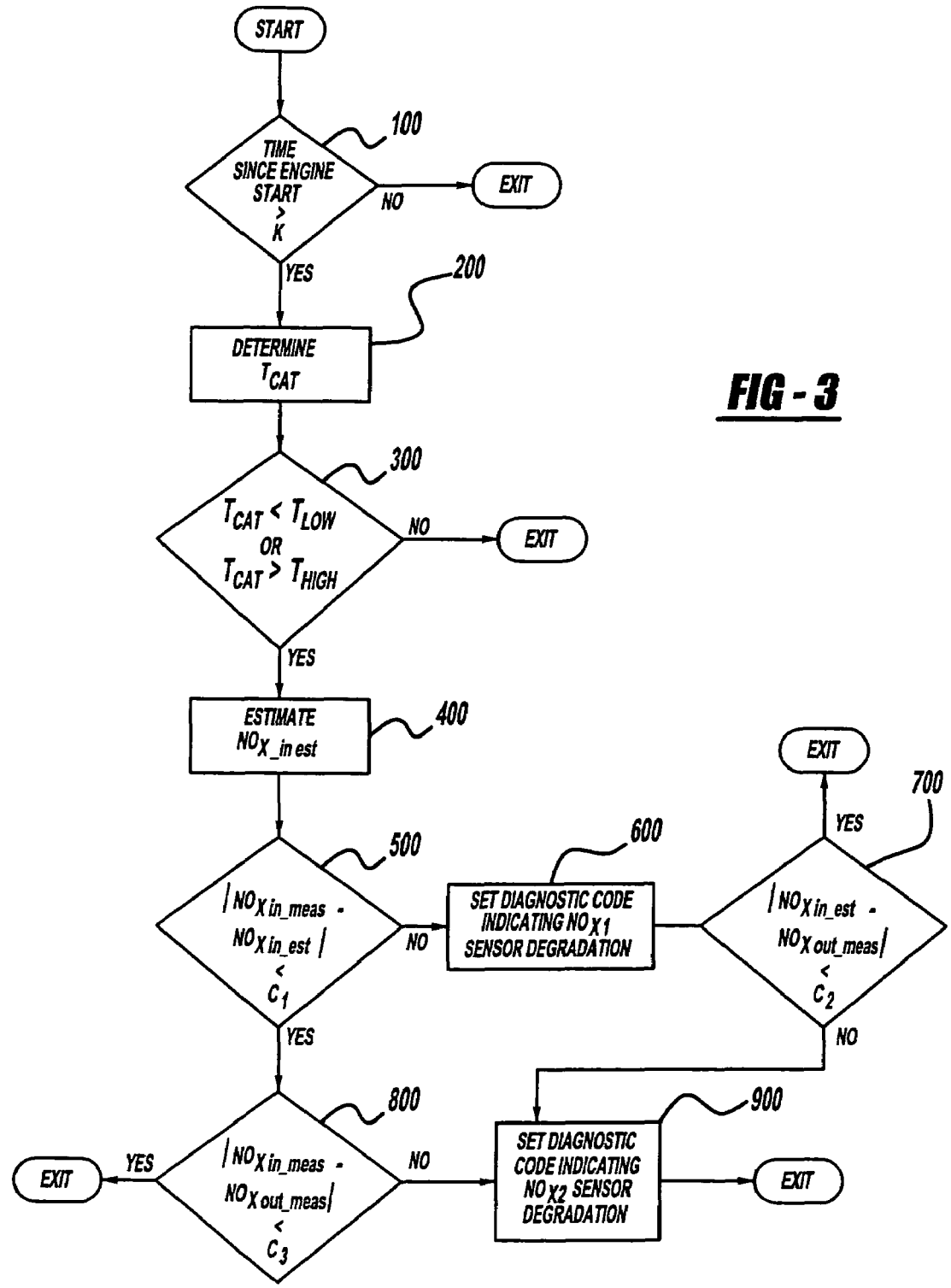
FIG. 3 is a high level flowchart of an exemplary embodiment of the present invention.

Referring now to FIG. 3, an exemplary routine for diagnosing degradation of an emission control system in accordance with the present invention is presented. As will be appreciated by one of ordinary skill in the art, the routine may represent one or more of any number of processing strategies such as event-driven, interrupt-driven, multi-tasking, multi-threading, and the like. As such, various steps or functions illustrated may be performed in the sequence illustrated, in parallel, or in some cases omitted. Likewise, the order of processing is not necessarily required to achieve the objects, features and advantages of the invention, but is provided for ease of illustration and description. Although not explicitly illustrated, one of ordinary skill in the art will recognize that one or more of the illustrated steps or functions may be repeatedly performed depending on the particular strategy being used.

Proceeding now with FIG. 3, first, in step 100, a determination is made whether a predetermined amount of time has elapsed since engine start. This condition is placed to ensure that the NOx sensors upstream and downstream have had a sufficient time to warm up and become fully operational. If the answer to step 100 is NO, the routine exits. If the answer to step 100 is YES, indicating that NOx sensors are operational, the routine proceeds to step 200 wherein catalyst temperature is determined as a function of temperature measurements upstream and downstream of the catalyst:

$$T_{out} = f(T_{in}, T_{out})$$

Next, in step 300, a determination is made whether catalyst temperature is lower than $T_{low}$ (e.g. below 150° C. for an SCR catalyst) or higher than $T_{high}$, (e.g., above 450° C. for an SCR catalyst) which are temperature ranges wherein NOx conversion efficiency of the catalyst is substantially zero. In other words, NOx conversion efficiency of a catalyst is substantially zero when its temperature is below a predetermined low threshold (such as during cold start) or above a predetermined high threshold (for example, following regeneration). Further, when the catalyst temperature is above $T_{high}$, all of the ammonia stored on the catalyst has been boiled off and therefore, catalyst NOx conversion efficiency is not affected by its release. If the answer to step 300 is NO, diagnostic conditions are not met, and the routine exits. If the answer to step 300 is YES, indicating that the catalyst temperature is within a range where its NOx conversion efficiency is substantially zero, the diagnostic routine proceeds to step 400 wherein $NOx_{in\_est}$, an estimate of an amount of NOx in the exhaust gas entering the catalyst is determined based on engine speed, load, exhaust gas temperature or any other parameter known to those skilled in the art to affect engine NOx production. The routine then proceeds to step 500 wherein a determination is made whether the difference between the $NOx_1$ sensor measurement, $NOx_{in\_meas}$, and the estimate, $NOx_{in\_est}$, is less than a small predetermined value $C_1$. If the answer to step 500 is NO, indicating there is a significant discrepancy between the measured and estimated values of the upstream NOx, the routine proceeds to step 600 wherein a diagnostic code indicating degradation of the upstream $NOx_1$ sensor is set. The routine then proceeds to step 700 wherein a determination is made whether the difference between $NOx_{in\_est}$ and the $NOx_2$ sensor measurement, $NOx_{out\_meas}$, is less than a small predetermined value $C_2$. If the answer to step 700 is YES, indicating that the downstream NOx sensor is not degraded, the routine exits. If the answer to step 700 is NO, the routine proceeds to step 900 wherein a diagnostic code indicating degradation of the $NOx_2$ sensor is set. The routine then exits.

If the answer to step 500 is YES, indicating that the upstream NOx sensor is not degraded, the routine proceeds to step 800 wherein a determination is made whether the difference between the $NOx_1$ sensor measurement and the $NOx_2$ sensor measurement is less than a small predetermined value $C_3$. If the answer to step 800 is YES, indicating that the two measurements are within a small, predetermined threshold of each other, the routine exits. If the answer to step 800 is NO, indicating that the downstream NOx sensor performance is degraded, the routine proceeds to step 900.

Therefore, according to the present invention, it is possible to diagnose degradation of the upstream NOx sensor by comparing its signal with an estimate of an amount of NOx upstream of the catalyst. This portion of the diagnostic routine can be performed at any catalyst temperature as long as the sensors themselves are sufficiently heated up to become operational.

Further, once a determination is made that the upstream NOx sensor is functioning, degradation in the downstream NOx sensor can be diagnosed by comparing the signals from the upstream and the downstream NOx sensors, when the catalyst temperature is such that its NOx conversion efficiency is substantially zero. If the difference between the two measurements is greater than a small, predetermined value, the downstream NOx sensor degradation is indicated.

In an alternative embodiment (not shown), the upstream NOx sensor may be eliminated, and an estimate of an amount of NOx in an exhaust gas mixture entering the catalyst may be obtained based on engine operating conditions. With such an embodiment, degradation of the downstream NOx sensor may be detected by comparing the estimate to the downstream NOx sensor measurement when the temperature of the catalyst is such that its NOx conversion efficiency is substantially zero. This method can also be used when the upstream NOx sensor is present, but has been diagnosed as degraded.

In yet another alternative embodiment (not shown), the NOx catalyst may be a lean NOx trap (LNT) and the temperature range wherein the diagnostic routine takes place is an LNT temperature at which substantially no NOx conversion or adsorption takes place (e.g. at temperatures above 450° C.).

This concludes the description of the invention. The reading of it by those skilled in the art would bring to mind many alterations and modifications without departing from the spirit and the scope of the invention. Accordingly, it is intended that the scope of the invention be defined by the following claims.

What is claimed is:

1. A method for diagnosing degradation of an emission control system coupled downstream of an internal combustion engine, the system including a NOx catalyst having a first NOx sensor coupled upstream of the catalyst and a second NOx sensor coupled downstream of the catalyst, the method comprising:

providing an indication of an operating condition;

in response to said indication diagnosing the first NOx sensor degradation if a difference between a first NOx sensor signal and an estimated amount of NOx in an exhaust gas mixture upstream of the catalyst is greater than a first predetermined value; and diagnosing the second NOx sensor degradation if a difference between a first NOx sensor signal and an estimated amount of NOx in an exhaust gas mixture upstream of the catalyst is less than said first predetermined value and a difference between said first NOx sensor signal and a second NOx sensor signal is greater than a second predetermined value.

2. The method as set forth in claim 1 wherein the NOx catalyst is an SCR catalyst.

3. The method as set forth in claim 1 wherein the NOx catalyst is an ALNC catalyst.

4. The method as set forth in claim 1 wherein said NOx catalyst is an LNT.

5. The method as set forth in claim 4 wherein said operating condition is a temperature of said LNT wherein there is substantially no NOx conversion or adsorption in said LNT.

6. The method as set forth in claim 1 wherein said operating condition is a catalyst temperature below 150° C.

7. The method as set forth in claim 1 wherein said operating condition is a catalyst temperature greater than 450° C.

8. A method for diagnosing degradation of a lean exhaust gas aftertreatment system, the system including a NOx catalyst having a first NOx sensor coupled upstream of the catalyst and a second NOx sensor coupled downstream of the catalyst, the method comprising:

comparing a first NOx sensor measurement and a second NOx sensor measurement when the catalyst is within a temperature range wherein a NOx conversion efficiency of the catalyst is substantially zero; and providing an indication of system degradation when a difference between said first NOx sensor measurement and said second sensor measurement is greater than a predetermined value.

9. A method for diagnosing degradation of a lean exhaust gas aftertreatment system, the system including a Lean NOx Trap (LNT) having a first NOx sensor coupled upstream of the LNT and a second NOx sensor coupled downstream of the LNT, the method comprising:

comparing a first NOx sensor measurement and a second NOx sensor measurement when the catalyst is within a temperature range wherein there is substantially no NOx conversion or adsorption in the LNT; and providing an indication of system degradation when a difference between said first NOx sensor measurement and said second sensor measurement is greater than a second predetermined value.

* * * * *